US010821124B2

(12) United States Patent
Sprenger et al.

(10) Patent No.: US 10,821,124 B2
(45) Date of Patent: Nov. 3, 2020

(54) COMPOSITIONS FOR USE IN IMPROVING STOOL CONSISTENCY OR FREQUENCY IN INFANTS OR YOUNG CHILDREN (71) Applicant: NESTEC S.A., Vevey (CH)

(72) Inventors: Norbert Sprenger, Savigny (CH); Dominique Brassart, Chavannes-pres-Renens (CH); Delphine Egli, La Tour-de-Peilz (CH)

(73) Assignee: Societe des Produits Nestle S.A., Vevey (CH)

( * ) Notice: Subject to any disclaimer, the term of this patent is extended or adjusted under 35 U.S.C. 154(b) by 0 days.

(21) Appl. No.: 15/554,738

(22) PCT Filed: Mar. 4, 2016

(86) PCT No.: PCT/EP2016/054614
§ 371 (c)(1),
(2) Date: Aug. 31, 2017

(87) PCT Pub. No.: WO2016/139330
PCT Pub. Date: Sep. 9, 2016

(65) Prior Publication Data
US 2018/0078573 A1 Mar. 22, 2018

(30) Foreign Application Priority Data
Mar. 5, 2015 (EP) .................... 15157724

(51) Int. Cl.
A61K 31/702 (2006.01)
A61P 1/00 (2006.01)
A23L 33/00 (2016.01)
A23L 33/135 (2016.01)
A23L 33/21 (2016.01)
A23L 33/125 (2016.01)
A61K 9/00 (2006.01)
A61K 35/741 (2015.01)
A61K 35/00 (2006.01)

(52) U.S. Cl.
CPC .......... A61K 31/702 (2013.01); A23L 33/125 (2016.08); A23L 33/135 (2016.08); A23L 33/21 (2016.08); A23L 33/40 (2016.08); A61K 9/0056 (2013.01); A61K 35/741 (2013.01); A61P 1/00 (2018.01); A23V 2002/00 (2013.01); A61K 2035/115 (2013.01)

(58) Field of Classification Search
None
See application file for complete search history.

(56) References Cited

U.S. PATENT DOCUMENTS 8,771,674 B2* 7/2014 Sprenger ............. A61K 31/702 424/93.4
9,217,133 B2* 12/2015 Sprenger ............. A61K 31/702
9,567,361 B2* 2/2017 Newburg ................ C07H 3/06
9,763,465 B2* 9/2017 Sprenger ................ A23L 33/10
9,854,826 B2* 1/2018 Sprenger ............. A61K 31/702
2009/0305996 A1 12/2009 Beermann et al.
2010/0216740 A1* 8/2010 Stahl ...................... A23L 7/198 514/54
2011/0207659 A1 8/2011 Morrow et al.
2012/0172319 A1* 7/2012 Chow ...................... A23L 33/40 514/21.92
2013/0236423 A1 9/2013 Sprenger et al.
2014/0371173 A1* 12/2014 Frantz ................ A61K 31/7016 514/61
2016/0287618 A1* 10/2016 Sprenger ................ A61K 45/06
2016/0296543 A1* 10/2016 Brassart ................ A23L 33/125
2016/0346303 A1* 12/2016 Hennet ............... A61K 31/7004
2017/0295838 A1* 10/2017 Destaillats ........... A61K 31/702
2017/0333462 A1* 11/2017 De Castro ............... A23L 33/40
2018/0036323 A1* 2/2018 Sprenger ................ A23L 33/40
2018/0042949 A1* 2/2018 Sprenger ............. A61K 31/702
2018/0078572 A1* 3/2018 Sprenger ............. A61K 31/702
2018/0220690 A1* 8/2018 Berger ............... A61K 31/7028
2019/0015436 A1* 1/2019 Binia .................... A61K 31/702

FOREIGN PATENT DOCUMENTS

CN 102946742 A 2/2013
EP 2842560 A1 3/2015
WO WO2011/012655 * 2/2011 ............. A61K 35/74

OTHER PUBLICATIONS

U.S. Appl. No. 16/071,736, filed Jul. 2018, Binia et al.*
U.S. Appl. No. 16/071,697, filed Jul. 2018, Binia et al.*
U.S. Appl. No. 16/071,696, filed Jul. 2018, Binia et al.*
U.S. Appl. No. 16/071,324, filed Jul. 2016, Binia et al.*
Chaturvedi et al., "Fucosylated human milk oligosaccharides vary between individuals and over the course of lactation" Glycobiology vol. 11 No. 5 pp. 365-372 (Year: 2001).*
Lara-Villoslada et al., "Beneficial effects of probiotic bacteria isolated from breast milk" British Journal of Nutrition vol. 98 suppl. 1 pp. S96-S100 (Year: 2007).*
Lee et al., "Whole cell biosynthesis of a functional oligosaccharide, 2'-fucosyllactose, using engineered *Escherichia coli*" Microbial Cell Factories vol. 11 No. 48 pp. 1-9 (Year: 2012).*
Coccorullo et al., "Lactobacillus reuteri (DSM 17938) in Infants with Functional Chronic Constipation: A Double-Blind, Randomized, Placebo-Controlled Study" The Journal of Pediatrics vol. 157 No. 4 pp. 598-602 (Year: 2010).*
Loening-Baucke et al., "Prevalence, Symptoms and Outcome of Constipation in Infants and Toddlers" Journal of Pediatrics vol. 146 pp. 359-363 (Year: 2005).*

(Continued)

Primary Examiner — Eric Olson
(74) Attorney, Agent, or Firm — K&L Gates LLP (57) ABSTRACT The present invention relates to a nutritional composition comprising at least one fucosylated oligosaccharide for use in preventing and/or treating constipation and/or in improving stool consistency/frequency in an infant or a young child.

11 Claims, 3 Drawing Sheets (56) References Cited

OTHER PUBLICATIONS

Besedovsky et al., "Across the Developmental Continuum of Irritable Bowel Syndrome: Clinical and Pathophysiologic Considerations" Current Gastroenterology Reports vol. 6 pp. 247-253 (Year: 2004).*
Chichlowski et al., "The Influence of Milk Oligosaccharides on Microbiota of Infants: Opportunities for Formulas" Annual Reviews on Food Science and Technology vol. 2 pp. 331-351 (Year: 2011).*
Marriage et al. "Infants Fed a Lower Calorie Formula With 2'FL Show Growth and 2'FL Uptake Like Breast-Fed Infants" JPGN, Dec. 2015, vol. 61, No. 6, pp. 649-658.
Russian Office Action for Appl No. 2017134672/10(060907) dated Aug. 20, 2019.
Chinese Office Action for Appl No. 201680014476.8 dated Jul. 3, 2020.

* cited by examiner

COMPOSITIONS FOR USE IN IMPROVING STOOL CONSISTENCY OR FREQUENCY IN INFANTS OR YOUNG CHILDREN

CROSS REFERENCE TO RELATED APPLICATIONS

The present application is a National Stage of International Application No. PCT/EP2016/054614, filed on Mar. 4, 2016, which claims priority to European Patent Application No. 15157724.4, filed on Mar. 5, 2015, the entire contents of which are being incorporated herein by reference.

FIELD OF THE INVENTION

This invention relates to compositions for use in preventing and/or treating constipation, in improving stool consistency/frequency, and/or in preventing or treating flatulence, bloating, colics or gut discomfort in infants or young children.

BACKGROUND OF THE INVENTION

Mother's milk is recommended for all infants. However, in some cases breast feeding is inadequate or unsuccessful for medical reasons or the mother chooses not to breast feed. Infant formula have been developed for these situations. Fortifiers have also been developed to enrich mother's milk or infant formula with specific ingredients. Infants and young children may suffer from constipation or hard stool due, especially, to the immaturity of their gut, the lack of activity at this young age and the undiversified content of their feeding. Because of their beneficial effects, prebiotics are therefore often incorporated into infant formula, fortifiers or any other synthetic nutritional compositions and nutritional supplements.

Prebiotics are non-digestible carbohydrates that contribute to the well-being of their host. They are typically compounds that pass undigested through the upper part of the gastrointestinal tract and stimulate the growth and/or activity of advantageous bacteria such as bifidobacteria that colonize the large bowel by acting as substrate for them. They will form the basis for stool.

However, some fibers including the beneficial prebiotics inulin and oligofructose, produce gases that fertilize the healthy bacteria that live in the lower gut. This may lead to flatulence, bloating, colics and/or gut discomfort in the individual. These associated effects may be particularly problematic in infants and young children and can lead to crying periods, feeding difficulties, irritability, pain, especially abdominal pain, abdominal cramping, poor sleep.

Human milk oligosaccharides (HMOs) are, collectively, the third largest solid constituents in human milk, after lactose and fat. HMOs usually consist of lactose at the reducing end with a carbohydrate core that often contains a fucose or a sialic acid at the non-reducing end. There are over one hundred milk oligosaccharides that have been isolated and characterized in human milk.

Some compositions using HMO ingredients, such as fucosylated oligosaccharides, lacto-N-tetraose, lacto-N-neotetraose and/or sialylated oligosaccharides, have been developed and for different purposes.

For example WO2005055944 from Children's hospital medical center describes a pharmaceutical composition comprising a molecule comprising a fucose group in an alpha-2 linkage, an alpha-3 linkage or an alpha-4 linkage to a galactose group and a pharmaceutically acceptable carrier. Various molecules are described such as 2'-fucosyllactose. This application is quite general since several infections can be prevented or treated, including respiratory or enteric infections, and there is a large target of patients (infants, children or adults). In addition, this document suggests that providing 2FL in medium or high amounts decreases the incidence of *Campylobacter* diarrhea.

WO9956754 from Abbott relates to compositions containing at least one fucose residue in an alpha 1-2 linkage such as 2FL and uses thereof. In particular, such compositions can be used in the treatment and prevention of gastrointestinal infections like diarrhoea and enterocolitis.

WO2004002495 describes an oligosaccharide-containing substance or receptor binding to diarrheagenic *Escherichia coli* and/or zoonotic *Helicobacter* species, and use thereof in, e.g., pharmaceutical, nutritional and other compositions for prophylaxis and treatment of diarrhea, hemorrhagic colitis or haemolytic uremic syndrome.

WO2012092156 refer to nutritional composition comprising HMOs but for a wide list of health benefits including feeding tolerance and especially reduction of diarrhea and loose stools (so the opposite of constipation), as well as reduction of the associated gas and colics.

Indeed, as indicated in Simone Albrecht et al "Oligosaccharides in feces of breast- and formula-fed babies", 2005, prebiotic cabohydrates (e.g. HMOs, GOS) have an impact on the neonatal gut development. However, the effects are specific to the types of fibers (HMOs and GOS are structurally different). For example, HMOs have been shown to facilitate a protective gut colonization in newborn infants (Riccardo Locascio et al, 2007, reference 2 of this publication) and also to confer a protection against diarrhea (Newburg et al, 2004, reference 5 of this publication).

None of the previous work is therefore focused on the prevention and/or treatment of constipation and/or the improvement of stool consistency/frequency without the above-mentioned associated problems of flatulence, bloating, colics and/or gut discomfort that can be particularly painful in infants and young children.

There is clearly a need for developing suitable methods to decrease the incidence of these health conditions/problems in infants and young children and especially there is a need for nutritional compositions such as infant formula that can provide softer stool without increasing flatulence, bloating, colics and/or gut discomfort.

There is also a need to deliver such health benefits in a manner that is particularly suitable for the young subjects (infants and young children), in a manner that does not involve a classical pharmaceutical intervention as these infants or young children are particularly fragile.

There is a need to deliver such health benefits in these infants or young children in a manner that does not induce side effects and/or in a manner that is easy to deliver, and well accepted by the parents or health care practitioners.

There is also a need to deliver such benefits in a manner that does keep the cost of such delivery reasonable and affordable by most.

SUMMARY OF THE INVENTION

The present inventors have found that a composition comprising at least one fucosylated oligosaccharide can advantageously be used to improve stool consistency in an infant or a young child, especially by reducing stool hardness.

Accordingly, the present invention therefore provides a nutritional composition comprising at least one fucosylated oligosaccharide for use in preventing and/or treating constipation, in improving stool consistency/frequency, in preventing and/or treating flatulence, bloating, colics and/or gut discomfort in an infant or a young child.

In some embodiments, the nutritional composition comprises at least a probiotic microorganism, especially a probiotic bacteria that may be of the following genera: *Lactobacillus* spp., *Streptococcus* spp., *Enterococcus* spp. or *Bifidobacterium* spp. In some preferred embodiments, the probiotic bacteria is a *Lactobacillus* strain.

In a particularly advantageous embodiment, the nutritional composition comprises 2'-fucosyllactose (2-FL) in an amount of 0.2-3 g/L of the nutritional composition.

FIGURES

FIG. 1 represent the stool consistency at 1 month of age (FIG. 1 A) and 2 months of age (FIG. 1 B) in infants fed a classical starter infant formula or a classical starter infant formula with HMO i.e. 2'Fucosyllactose in an amount of 1.24 g/L and lacto-N-neotetraose in an amount of 0.63 g/L. Numbers indicate stool consistency according to the Bristol scale: 1: Separate Hard lumps, like nuts (hard to pass). Result in slow transit, 2: Sausage-shaped but lumpy, 3: Like a sausage but with cracks on its surface, 4: Like a sausage or snake-smooth and soft, 5: Soft blobs with clear cue edges (easy to pass), 6: Fluffy pieces with ragged edges, a mushy stool, 7: Watery, no solid pieces.

DETAILED DESCRIPTION OF THE INVENTION

As used herein, the following terms have the following meanings.

The term "infant" means a child under the age of 12 months.

The expression "young child" means a child aged between one and three years, also called toddler.

An "infant or young child born by C-section" means an infant or young child who was delivered by caesarean. It means that the infant or young child was not vaginally delivered.

An "infant or young child vaginally born" means an infant or young child who was vaginally delivered and not delivered by caesarean.

A "preterm" or "premature" means an infant or young child who was not born at term. Generally it refers to an infant or young child born prior 36 weeks of gestation.

The expression "nutritional composition" means a composition which nourishes a subject. This nutritional composition is usually to be taken orally or intravenously, and it usually includes a lipid or fat source and a protein source.

In a particular embodiment the composition of the present invention is a hypoallergenic nutritional composition. The expression "hypoallergenic nutritional composition" means a nutritional composition which is unlikely to cause allergic reactions.

In a particular embodiment the composition of the present invention is a "synthetic nutritional composition". The expression "synthetic nutritional composition" means a mixture obtained by chemical and/or biological means, which can be chemically identical to the mixture naturally occurring in mammalian milks (i.e. the synthetic composition is not breast milk).

The expression "infant formula" as used herein refers to a foodstuff intended for particular nutritional use by infants during the first months of life and satisfying by itself the nutritional requirements of this category of person (Article 2(c) of the European Commission Directive 91/321/EEC 2006/141/EC of 22 Dec. 2006 on infant formulae and follow-on formulae). It also refers to a nutritional composition intended for infants and as defined in Codex Alimentarius (Codex STAN 72-1981) and Infant Specialities (incl. Food for Special Medical Purpose). The expression "infant formula" encompasses both "starter infant formula" and "follow-up formula" or "follow-on formula".

A "follow-up formula" or "follow-on formula" is given from the 6th month onwards. It constitutes the principal liquid element in the progressively diversified diet of this category of person.

The expression "baby food" means a foodstuff intended for particular nutritional use by infants or young children during the first years of life.

The expression "infant cereal composition" means a foodstuff intended for particular nutritional use by infants or young children during the first years of life.

The term "fortifier" refers to liquid or solid nutritional compositions suitable for mixing with breast milk or infant formula.

The expression "weaning period" means the period during which the mother's milk is substituted by other food in the diet of an infant or young child.

The expressions "days/weeks/months/years of life" and "days/weeks/months/years of birth" can be used interchangeably.

The expression "preventing and/or treating constipation and/or improving stool consistency/frequency" encompasses one or several of the following:
preventing constipation
treating constipation
improving stool consistency
improving stool frequency.

The expression "preventing and/or treating flatulence, bloating, colics and/or gut discomfort" encompasses one or several of the following:
preventing flatulence
treating flatulence
preventing bloating
treating bloating
preventing colics
treating colics
preventing gut discomfort
treating gut discomfort.

The expressions "in preventing constipation/flatulence/bloating/colics/gut discomfort", "to prevent constipation/flatulence/bloating/colics/gut discomfort", "in the prevention of constipation/flatulence/bloating/colics/gut discomfort" and "for the prevention of constipation/flatulence/bloating/colics/gut discomfort" can be used interchangeably.

These expressions mean avoiding that these health conditions/issues (constipation/flatulence/bloating/colics/gut discomfort) occur and/or decreasing the incidence of said health conditions/issues (reduction of the frequency, i.e. the number of these health conditions/issues). In some embodiments the prevention of these health conditions/issues occurs during the treatment (i.e. during the administration of the composition of the present invention, either immediately after the start of the administration or some time after, e.g. some days or weeks after the start). It can also encompass the prevention of these health conditions/issues later in life. The term "later in life" encompasses the effect after the termination of the intervention or treatment. The effect "later in life" can be from 1 week to several months, for example from 2 to 4 weeks, from 2 to 6 weeks, from 2 to 8 weeks, from 1 to 6 months or from 2 to 12 months.

The expressions "in treating constipation/flatulence/bloating/colics/gut discomfort", "to treat constipation/flatulence/bloating/colics/gut discomfort", "in the treatment of constipation/flatulence/bloating/colics/gut discomfort" and "for the treatment of constipation/flatulence/bloating/colics/gut discomfort" can be used interchangeably.

They should be understood as comprising the decrease of the duration of these health conditions/issues (constipation/flatulence/bloating/colics/gut discomfort) (e.g. number of days/weeks/years the infants or young children will suffer from these health conditions/issues), the decrease of the severity (or level) of these health conditions/issues (e.g. the consequences and/or the seriousness of these health conditions/issues). These expressions also encompass the relieve of the symptoms or consequences such as blocking stool, crying periods, feeding difficulties, irritability, pain, especially abdominal pain, abdominal cramping, poor sleep and any combinations thereof, and/or the decrease of complications caused by these health conditions/issues on the infant or young child health, such as anal fissure, rectal bleeding, the need of a surgical intervention, the use of medication, the use of stool softeners, and/or the decrease of pain, and/or the decrease of tiredness, and/or the ease of the sleep and/or the stabilization of the activity of the infants or young children suffering from these health conditions/issues.

The expressions "no or a limited level" and "no particular issue" of flatulence, bloating, colics and/or gut discomfort can be used interchangeably. They have to be understood in the context of the present invention that infants or young children fed the composition of the present invention will have no flatulence, bloating, colics and/or gut discomfort episodes or they will have a low level of flatulence, bloating, colics and/or gut discomfort or they will have less (e.g. at least 1% less, or at least 2% less, or at least 5% less, or at least 10% less, or at least 20% less or at least 50% less . . . ) flatulence, bloating, colics and/or gut discomfort episodes in comparison with infants or young children fed with a standard composition (e.g. the same composition but without any fucosylated oligosaccharide without any fucosylated oligosaccharide). The expressions "a limited level" and "a lower level" can be used interchangeably. They may refer to the frequency and/or the occurrence and/or the severity.

The terms "gut", "GUT" and "gastrointestinal" can be used interchangeably.

The expression "gut discomfort" includes abdominal pain and/or cramping.

The expressions "in improving stool consistency/frequency", "in improving stool consistency and/or frequency" and "in improving stool consistency and/or stool frequency" can be used interchangeably. They encompass the improvement of stool consistency, the improvement of stool frequency and/or both. The expression "improving stool consistency" means that the stool of an infant or young child feeding a nutritional composition according to the invention has a softer consistency than the stool of an infant or young child not feeding a nutritional composition according to the invention. The expression "improving stool consistency" may especially encompass or mean "reducing stool hardness", "softening stool" and/or "providing softer stool", e.g. there will be less hard lumps, like nuts, that are hard to pass.

The expression "improving stool frequency" means that the stool of an infant or young child will become more frequent, i.e. the transit will be regulated and/or faster. It may therefore also encompass or mean "improving/increasing the transit speed" or "avoiding a slow transit" or "regulating the transit". The improvement of stool consistency/frequency may especially allow avoiding pain, especially abdominal pain, abdominal cramping and also further complications like anal fissure, rectal bleeding, the need of a surgical intervention, the use of medication, the use of stool softeners.

The "mother's milk" should be understood as the breast milk or the colostrum of the mother.

An "oligosaccharide" is a saccharide polymer containing a small number (typically three to ten) of simple sugars (monosaccharides).

The term "HMO" or "HMOs" refers to human milk oligosaccharide(s). These carbohydrates are highly resistant to enzymatic hydrolysis, indicating that they may display essential functions not directly related to their caloric value. It has especially been illustrated that they play a vital role in the early development of infants and young children, such as the maturation of the immune system. Many different kinds of HMOs are found in the human milk. Each individual oligosaccharide is based on a combination of glucose, galactose, sialic acid (N-acetylneuraminic acid), fucose and/or N-acetylglucosamine with many and varied linkages between them, thus accounting for the enormous number of different oligosaccharides in human milk—over 130 such structures have been identified so far. Almost all of them have a lactose moiety at their reducing end while sialic acid and/or fucose (when present) occupy terminal positions at the non-reducing ends. The HMOs can be acidic (e.g. charged sialic acid containing oligosaccharide) or neutral (e.g. fucosylated oligosaccharide).

A "fucosylated oligosaccharide" is an oligosaccharide having a fucose residue. It has a neutral nature. Some examples are 2-FL (2'-fucosyllactose), 3-FL (3-fucosyllactose), difucosyllactose, lacto-N-fucopentaose (e.g. lacto-N-fucopentaose I, lacto-N-fucopentaose II, lacto-N-fucopentaose III, lacto-N-fucopentaose V), lacto-N-fucohexaose, lacto-N-difucohexaose I, fucosyllacto-N-hexaose, fucosyllacto-N-neohexaose, difucosyllacto-N-hexaose I, difucosyllacto-N-neohexaose II and any combination thereof.

The expressions "fucosylated oligosaccharides comprising a 2'-fucosyl-epitope" and "2-fucosylated oligosaccharides" encompass fucosylated oligosaccharides with a certain homology of form since they contain a 2'-fucosyl-epitope, therefore a certain homology of function can be expected.

The expression "N-acetylated oligosaccharide(s)" encompasses both "N-acetyl-lactosamine" and "oligosaccharide(s) containing N-acetyl-lactosamine". They are neutral oligosaccharides having an N-acetyl-lactosamine residue. Suitable examples are LNT (lacto-N-tetraose), para-lacto-N-neohexaose (para-LNnH), LNnT (lacto-N-neotetraose) or any combination thereof. Other examples are lacto-N-hexaose, lacto-N-neohexaose, para-lacto-N-hexaose, para-lacto-N-neohexaose, lacto-N-octaose, lacto-N-neooctaose, iso-lacto-N-octaose, para-lacto-N-octaose and lacto-N-decaose.

A "precursor of HMO" is a key compound that intervenes in the manufacture of HMO, such as sialic acid and/or fucose.

A "sialylated oligosaccharide" is a charged sialic acid containing oligosaccharide, i.e. an oligosaccharide having a sialic acid residue. It has an acidic nature. Some examples are 3-SL (3' sialyllactose) and 6-SL (6' sialyllactose).

The nutritional composition of the present invention can be in solid form (e.g. powder) or in liquid form. The amount of the various ingredients (e.g. the oligosaccharides) can be expressed in g/100 g of composition on a dry weight basis when it is in a solid form, e.g. a powder, or as a concentration in g/L of the composition when it refers to a liquid form (this latter also encompasses liquid composition that may be obtained from a powder after reconstitution in a liquid such as milk, water . . . , e.g. a reconstituted infant formula or follow-on/follow-up formula or infant cereal product or any other formulation designed for infant nutrition).

The term "prebiotic" means non-digestible carbohydrates that beneficially affect the host by selectively stimulating the growth and/or the activity of healthy bacteria such as bifidobacteria in the colon of humans (Gibson G R, Roberfroid M B. *Dietary modulation of the human colonic microbiota: introducing the concept of prebiotics. J Nutr.* 1995; 125:1401-12).

The term "probiotic" means microbial cell preparations or components of microbial cells with a beneficial effect on the health or well-being of the host. (Salminen S, Ouwehand A. Benno Y. et al. "*Probiotics: how should they be defined*" Trends Food Sci. Technol. 1999:10 107-10). The microbial cells are generally bacteria or yeasts.

The term "cfu" should be understood as colony-forming unit.

All percentages are by weight unless otherwise stated.

In addition, in the context of the invention, the terms "comprising" or "comprises" do not exclude other possible elements. The composition of the present invention, including the many embodiments described herein, can comprise, consist of, or consist essentially of the essential elements and limitations of the invention described herein, as well as any additional or optional ingredients, components, or limitations described herein or otherwise depending on the needs.

Any reference to prior art documents in this specification is not to be considered an admission that such prior art is widely known or forms part of the common general knowledge in the field.

The invention will now be described in further details. It is noted that the various aspects, features, examples and embodiments described in the present application may be compatible and/or combined together.

A first object of the present invention is therefore a nutritional composition comprising at least one fucosylated oligosaccharide, for use in preventing and/or treating constipation and/or in improving stool consistency/frequency in an infant or a young child.

In the same time, the nutritional composition can provide no or limited flatulence, bloating, colics and/or gut discomfort in said infant or young child.

Another object of the present invention is a nutritional composition comprising at least one fucosylated oligosaccharide for use in preventing and/or treating flatulence, bloating, colics and/or gut discomfort in an infant or a young child, and wherein the fucosylated oligosaccharide(s) is/are in a total amount of 0.8-1.5 g/L of the composition and/or in a total amount of 0.55-1.05 g/100 g of composition on a dry weight basis.

Without being bound by theory, the inventors of the present invention believe that the fucosylated oligosaccharide(s) is the key ingredient that surprisingly provides the above-mentioned health benefits.

Without being bound by theory, the inventors also believe that the observed effect is mediated via an alteration of the intestinal ecosystem, thus indirectly affecting stool consistency/frequency, bowel movements and eventually gut discomfort.

In some preferred embodiments, the nutritional composition comprises at least a probiotic microorganism, preferably at least one probiotic strain. Without being bound by theory, the inventors believe that the fucosylated oligosaccharide(s) and the probiotic microorganism(s) may act synergically to further provide the above-mentioned health benefits.

The composition of the present invention comprises at least one fucosylated oligosaccharide. There can be one or several types of fucosylated oligosaccharide(s). The fucosylated oligosaccharide(s) can indeed be selected from the list comprising 2'-fucosyl lactose, 3'fucosyllactose, difucosyllactose, lacto-N-fucopentaose (such as lacto-N-fucopentaose I, lacto-N-fucopentaose II, lacto-N-fucopentaose III, lacto-N-fucopentaose V), lacto-N-fucohexaose, lacto-N-difucohexaose I, fucosyllacto-N-hexaose, fucosyllacto-N-neohexaose (such as fucosyllacto-N-neohexaose I, fucosyllacto-N-neohexaose II), difucosyllacto-N-hexaose I, difuco-lacto-N-neohexaose, difucosyllacto-N-neohexaose I, difucosyllacto-N-neohexaose II, fucosyl-para-Lacto-N-hexaose, tri-fuco-para-Lacto-N-hexaose I and any combination thereof.

In some particular embodiments the fucosylated oligosaccharide comprises a 2'-fucosyl-epitope. It can be for example selected from the list comprising 2'-fucosyllactose, difucosyllactose, lacto-N-fucopentaose, lacto-N-fucohexaose, lacto-N-difucohexaose, fucosyllacto-N-hexaose, fucosyllacto-N-neohexaose, difucosyllacto-N-hexaose difuco-lacto-N-neohexaose, difucosyllacto-N-neohexaose, fucosyl-para-Lacto-N-hexaose and any combination thereof.

In a preferred embodiment, the nutritional composition according to the invention comprises 2'-fucosyllactose (or 2FL, or 2'FL, or 2-FL or 2'-FL). In a particular embodiment, there is no other type of fucosylated oligosaccharide than 2'-fucosyllactose, i.e. the nutritional composition of the invention comprises only 2'-fucosyllactose as fucosylated oligosaccharide.

The fucosylated oligosaccharide(s) may be isolated by chromatography or filtration technology from a natural source such as animal milks. Alternatively, it may be produced by biotechnological means using specific fucosyltransferases and/or fucosidases either through the use of enzyme-based fermentation technology (recombinant or natural enzymes) or microbial fermentation technology. In the latter case, microbes may either express their natural enzymes and substrates or may be engineered to produce respective substrates and enzymes. Single microbial cultures and/or mixed cultures may be used. Fucosylated oligosaccharide formation can be initiated by acceptor substrates starting from any degree of polymerization (DP), from DP=1 onwards. Alternatively, fucosylated oligosaccharides may be produced by chemical synthesis from lactose and free fucose. Fucosylated oligosaccharides are also available for example from Kyowa, Hakko, Kogyo of Japan.

The fucosylated oligosaccharide(s) can be present in the nutritional composition according to the present invention in a total amount of 0.2-3 g/L, for example 0.5-2 g/L or 0.75-1.65 g/L of the composition. In some embodiments, the fucosylated oligosaccharide(s) may be in a total amount of 0.8-1.5 g/L of the composition, such as 0.85-1.3 g/L or 0.9-1.25 g/L or 0.9-1.1 g/L or 1-1.25 g/L or 1.05-1.25 g/L of the composition. In a particular embodiment, the fucosylated oligosaccharide(s) is/are in a total amount of 1 g/L of the composition. In another particular embodiment, the fucosylated oligosaccharide(s) is/are in a total amount of 1.24 g/L of the composition. The fucosylated oligosaccharide(s) can be present in the nutritional composition in a total amount of 0.13-2.1 g/100 g, for example 0.34-1.4 g/100 g or 0.52-1.15 g/100 g of composition on a dry weight basis. The fucosylated oligosaccharide(s) may be in a total amount of 0.55-1.05 g/100 g of the composition, such as 0.59-0.9 g/100 g, or 0.62-0.87 g/100 g or 0.62-0.77 g/100 g or 0.69-0.87 g/100 g or 0.73-0.87 g/100 g of the composition. In a particular embodiment, the fucosylated oligosaccharide(s) is/are in a total amount of 0.69 g/100 g of the composition. In another particular embodiment, the fucosylated oligosaccharide(s) is/are in a total amount of 0.86 g/100 g of the composition.

The nutritional composition according to the present invention may also comprise at least another oligosaccharide(s) (i.e. other than the fucosylated oligosaccharide(s) necessarily present in the composition) and/or at least a fiber(s) and/or at least a precursor(s) thereof. The other oligosaccharide and/or fiber and/or precursor thereof may be selected from the list comprising galacto-oligosaccharides (GOS), fructo-oligosaccharides (FOS), inulin, xylooligosaccharides (XOS), polydextrose, N-acetylated oligosaccharides, sialylated oligosaccharides, sialic acid, fucose and any combination thereof. They may be in an amount between 0 and 10% by weight of composition.

Suitable commercial products that can be used in addition to the oligosaccharides comprised in the oligosaccharide mixture to prepare the nutritional compositions according to the invention include combinations of FOS with inulin such as the product sold by BENEO under the trademark Orafti, or polydextrose sold by Tate & Lyle under the trademark STA-LITE®.

In some specific embodiments, the nutritional composition of the present invention may also comprise at least one the N-acetylated oligosaccharide. There can be one or several types of N-acetylated oligosaccharide. The N-acetylated oligosaccharide(s) can be for example lacto-N-tetraose (LNT), lacto-N-neotetraose (LNnT) or any combination thereof. In some particular embodiments the N-acetylated oligosaccharide is lacto-N-neotetraose (LNnT), para-lacto-N-neohexaose (para-LNnH) or any combination thereof. In some particular embodiments the N-acetylated oligosaccharide is LNnT. In some particular embodiments the N-acetylated oligosaccharide is LNT. In some other particular embodiments the N-acetylated oligosaccharide is a mixture of LNT and LNnT. In some particular embodiments the composition comprises both LNT and LNnT in a ratio LNT:LNnT between 5:1 and 1:2, or from 2:1 to 1:1, or from 2:1.2 to 2:1.6. The N-acetylated oligosaccharide(s) may be synthesised chemically by enzymatic transfer of saccharide units from donor moieties to acceptor moieties using glycosyltransferases as described for example in U.S. Pat. No. 5,288,637 and WO 96/10086. Alternatively, LNT and LNnT may be prepared by chemical conversion of Keto-hexoses (e.g. fructose) either free or bound to an oligosaccharide (e.g. lactulose) into N-acetylhexosamine or an N-acetyl-hexosamine-containing oligosaccharide as described in Wrodnigg, T. M.; Stutz, A. E. (1999) Angew. Chem. Int. Ed. 38:827-828. N-acetyl-lactosamine produced in this way may then be transferred to lactose as the acceptor moiety.

The N-acetylated oligosaccharide(s) can be present in the nutritional composition according to the present invention in a total amount of 0.1-2 g/L, for example 0.3-1 g/L or 0.45-0.85 g/L of the composition.

In some embodiments, the N-acetylated oligosaccharide(s) may be in a total amount of 0.5-0.8 g/L of the composition, such as 0.5-0.75 g/L or 0.5-0.7 g/L of the composition. In a particular embodiment, the N-acetylated oligosaccharide(s) is/are in a total amount of 0.5 g/L of the composition. In another particular embodiment, the N-acetylated oligosaccharide(s) is/are in a total amount of 0.63 g/L of the composition.

The N-acetylated oligosaccharide(s) can be present in the nutritional composition in a total amount of 0.06-1.4 g/100 g, for example 0.2-0.7 g/100 g or 0.31-0.59 g/100 g of composition on a dry weight basis, The N-acetylated oligosaccharide(s) may be in a total amount of 0.35-0.56 g/100 g of composition, such as 0.35-0.52 g/100 g or 0.35-0.49 g/100 g. In a particular embodiment, the N-acetylated oligosaccharide(s) is/are in a total amount of 0.35 g/100 g of the composition. In another particular embodiment, the N-acetylated oligosaccharide(s) is/are in a total amount of 0.44 g/100 g of the composition.

In some embodiments, the nutritional composition comprises both 2'-fucosyllactose (2-FL) and lacto-N-neotetraose (LNnT). In another specific embodiment, the nutritional composition of the present invention comprises an oligosaccharide mixture that consists of 2'-fucosyllactose (2-FL) and lacto-N-neotetraose (LNnT). In other words, the nutritional composition of the invention comprises only 2'-fucosyllactose (2-FL) as fucosylated oligosaccharide and only lacto-N-neotetraose (LNnT) as N-acetylated oligosaccharide.

The nutritional composition can comprise fucosylated oligosaccharide(s) and N-acetylated oligosaccharide(s) in a ratio fucosylated oligosaccharide(s):the N-acetylated oligosaccharide(s) of from 2:0.065 to 2:20 such as from 2:0.3 to 2:4, for example 2:0.54 to 2:2.26, or 2:0.76-2:1.8 or 2:0.8-2:1.4. In a particularly advantageous embodiment, this ratio is 2:1 or around 2:1.

In some other particular embodiments, the nutritional composition according to the invention does not comprise any N-acetylated oligosaccharides.

In a particular embodiment, the composition according to the invention can comprise sialylated oligosaccharide(s). There can be one or several sialylated oligosaccharide(s).

The sialylated oligosaccharide(s) can be selected from the group comprising 3' sialyllactose (3-SL), 6' sialyllactose (6-SL), and any combination thereof. In some embodiments of the invention the composition comprises 3-SL and 6-SL. In some particular embodiments the ratio between 3'-sialyllactose (3-SL) and 6'-sialyllactose (6-SL) can be in the range between 5:1 and 1:10, or from 3:1 and 1:1, or from 1:1 to 1:10. In some specific embodiments the sialylated oligosaccharide of the composition is 6' sialyllactose (6-SL).

The sialylated oligosaccharide(s) may be isolated by chromatographic or filtration technology from a natural source such as animal milks. Alternatively, they may be produced by biotechnological means using specific sialyltransferases or sialidases, neuraminidases, either by an enzyme based fermentation technology (recombinant or natural enzymes), by chemical synthesis or by a microbial fermentation technology. In the latter case microbes may either express their natural enzymes and substrates or may be engineered to produce respective substrates and enzymes. Single microbial cultures or mixed cultures may be used. Sialyl-oligosaccharide formation can be initiated by acceptor substrates starting from any degree of polymerisation (DP), from DP=1 onwards. Alternatively, sialyllactoses may be produced by chemical synthesis from lactose and free N'-acetylneuraminic acid (sialic acid). Sialyllactoses are also commercially available for example from Kyowa Hakko Kogyo of Japan.

In particular examples the composition may comprise from 0.05 to 5 g/L of sialylated oligosaccharide(s), or from 0.1 to 4 g/L, or from 0.3 to 2 g/L, or from 0.4 to 1.5 g/L, or from 0.4 to 1 g/L, for example 0.5 or 0.9 g/L of sialylated oligosaccharide(s). In some particular embodiments the composition can comprise from 0.8 to 1.7 g/l of sialylated oligosaccharide(s).

The composition according to the invention can contain from 0.03 to 3.5 g of sialylated oligosaccharide(s) per 100 g of composition on a dry weight basis, e.g. from 0.1 to 2 g or from 0.2 to 1 g or form 0.3 to 0.6 g of sialylated oligosaccharide(s) per 100 g of composition on a dry weight basis.

In some particular embodiments of the present invention, the nutritional composition comprises sialylated oligosaccharide(s) in an amount of below 0.1 g/100 g of composition on a dry weight basis.

In some particular embodiments of the present invention, the nutritional composition does not contain any sialylated oligosaccharide(s).

In some other particular embodiments of the present invention, the nutritional composition does not contain any galacto-oligosaccharides (GOS).

In a particular embodiment, the nutritional composition can also contain at least one BMO (bovine milk oligosaccharide). In another particular embodiment, the nutritional composition does not comprise any bovine milk oligosaccharide.

The composition according to the present invention may optionally also comprise at least one precursor of oligosaccharide. There can be one or several precursor(s) of oligosaccharide. For example the precursor of human milk oligosaccharide is sialic acid, fucose or a mixture thereof. In some particular embodiments the composition comprises sialic acid.

In particular examples the composition comprises from 0 to 3 g/L of precursor(s) of oligosaccharide, or from 0 to 2 g/L, or from 0 to 1 g/L, or from 0 to 0.7 g/L, or from 0 to 0.5 g/L or from 0 to 0.3 g/L, or from 0 to 0.2 g/L of precursor(s) of oligosaccharide.

The composition according to the invention can contain from 0 to 2.1 g of precursor(s) of oligosaccharide per 100 g of composition on a dry weight basis, e.g. from 0 to 1.5 g or from 0 to 0.8 g or from 0 to 0.15 g of precursor(s) of oligosaccharide per 100 g of composition on a dry weight basis.

In preferred embodiments, the nutritional composition of the present invention can further comprise at least one probiotic microorganism, such as a probiotic bacterial strain.

The probiotic microorganisms most commonly used are principally bacteria and yeasts of the following genera: *Lactobacillus* spp., *Streptococcus* spp., *Enterococcus* spp., *Bifidobacterium* spp. and *Saccharomyces* spp.

In some particular embodiments, the probiotic is a probiotic bacterial strain. In some specific embodiments, it is particularly Lactobacilli. In a preferred embodiment, the nutritional composition comprises at least one *Lactobacillus* strain.

Suitable probiotic bacterial strains include *Lactobacillus rhamnosus* ATCC 53103 available from Valio Oy of Finland under the trademark LGG, *Lactobacillus rhamnosus* CGMCC 1.3724, *Lactobacillus paracasei* CNCM 1-2116, *Lactobacillus johnsonii* CNCM I-1225, *Streptococcus salivarius* DSM 13084 sold by BLIS Technologies Limited of New Zealand under the designation K12, *Bifidobacterium lactis* CNCM 1-3446 sold inter alia by the Christian Hansen company of Denmark under the trademark Bb 12, *Bifidobacterium longum* ATCC BAA-999 sold by Morinaga Milk Industry Co. Ltd. of Japan under the trademark BB536, *Bifidobacterium breve* sold by Danisco under the trademark Bb-03, *Bifidobacterium breve* sold by Morinaga under the trade mark M-16V, *Bifidobacterium infantis* sold by Procter & Gamble Co. under the trademark Bifantis and *Bifidobacterium breve* sold by Institut RoseII (Lallemand) under the trademark R0070.

The nutritional composition according to the invention may contain from 10e3 to 10e12 cfu of probiotic strain, more preferably between 10e7 and 10e12 cfu such as between 10e8 and 10e10 cfu of probiotic strain per g of composition on a dry weight basis.

In one embodiment the probiotics are viable. In another embodiment the probiotics are non-replicating or inactivated. There may be both viable probiotics and inactivated probiotics in some other embodiments.

The nutritional composition of the invention can further comprise at least one phage (bacteriophage) or a mixture of phages, preferably directed against pathogenic Streptococci, *Haemophilus, Moraxella* and Staphylococci.

The nutritional composition according to the invention can be for example an infant formula, a starter infant formula, a follow-on or follow-up formula, a baby food, an infant cereal composition, a fortifier such as a human milk fortifier, or a supplement. In some particular embodiments, the composition of the invention is an infant formula, a fortifier or a supplement that may be intended for the first 4 or 6 months of age. In a preferred embodiment the nutritional composition of the invention is an infant formula.

In some other embodiments the nutritional composition of the present invention is a fortifier. The fortifier can be a breast milk fortifier (e.g. a human milk fortifier) or a formula fortifier such as an infant formula fortifier or a follow-on/follow-up formula fortifier.

When the nutritional composition is a supplement, it can be provided in the form of unit doses.

The nutritional composition of the present invention can be in solid (e.g. powder), liquid or gelatinous form.

The nutritional composition according to the invention generally contains a protein source. The protein can be in an amount of from 1.6 to 3 g per 100 kcal. In some embodiments, especially when the composition is intended for premature infants, the protein amount can be between 2.4 and 4 g/100 kcal or more than 3.6 g/100 kcal. In some other embodiments the protein amount can be below 2.0 g per 100 kcal, e.g. between 1.8 to 2 g/100 kcal, or in an amount below 1.8 g per 100 kcal.

The type of protein is not believed to be critical to the present invention provided that the minimum requirements for essential amino acid content are met and satisfactory growth is ensured. Thus, protein sources based on whey, casein and mixtures thereof may be used as well as protein sources based on soy. As far as whey proteins are concerned, the protein source may be based on acid whey or sweet whey or mixtures thereof and may include alpha-lactalbumin and beta-lactoglobulin in any desired proportions.

In some advantageous embodiments the protein source is whey predominant (i.e. more than 50% of proteins are coming from whey proteins, such as 60% or 70%).

The proteins may be intact or hydrolysed or a mixture of intact and hydrolysed proteins. By the term "intact" is meant that the main part of the proteins are intact, i.e. the molecular structure is not altered, for example at least 80% of the proteins are not altered, such as at least 85% of the proteins are not altered, preferably at least 90% of the proteins are not altered, even more preferably at least 95% of the proteins are not altered, such as at least 98% of the proteins are not altered. In a particular embodiment, 100% of the proteins are not altered.

The term "hydrolysed" means in the context of the present invention a protein which has been hydrolysed or broken down into its component amino acids.

The proteins may be either fully or partially hydrolysed. It may be desirable to supply partially hydrolysed proteins (degree of hydrolysis between 2 and 20%), for example for infants or young children believed to be at risk of developing cow's milk allergy. If hydrolysed proteins are required, the hydrolysis process may be carried out as desired and as is known in the art. For example, whey protein hydrolysates may be prepared by enzymatically hydrolysing the whey fraction in one or more steps. If the whey fraction used as the starting material is substantially lactose free, it is found that the protein suffers much less lysine blockage during the hydrolysis process. This enables the extent of lysine blockage to be reduced from about 15% by weight of total lysine to less than about 10% by weight of lysine; for example about 7% by weight of lysine which greatly improves the nutritional quality of the protein source.

In an embodiment of the invention at least 70% of the proteins are hydrolysed, preferably at least 80% of the proteins are hydrolysed, such as at least 85% of the proteins are hydrolysed, even more preferably at least 90% of the proteins are hydrolysed, such as at least 95% of the proteins are hydrolysed, particularly at least 98% of the proteins are hydrolysed. In a particular embodiment, 100% of the proteins are hydrolysed.

In one particular embodiment the proteins of the nutritional composition are hydrolyzed, fully hydrolyzed or partially hydrolyzed. The degree of hydrolysis (DH) of the protein can be between 8 and 40, or between 20 and 60 or between 20 and 80 or more than 10, 20, 40, 60, 80 or 90.

In a particular embodiment the nutritional composition according to the invention is a hypoallergenic composition. In another particular embodiment the composition according to the invention is a hypoallergenic nutritional composition.

The nutritional composition according to the present invention generally contains a carbohydrate source. This is particularly preferable in the case where the nutritional composition of the invention is an infant formula. In this case, any carbohydrate source conventionally found in infant formulae such as lactose, sucrose, saccharose, maltodextrin, starch and mixtures thereof may be used although one of the preferred sources of carbohydrates is lactose.

The nutritional composition according to the present invention generally contains a source of lipids. This is particularly relevant if the nutritional composition of the invention is an infant formula. In this case, the lipid source may be any lipid or fat which is suitable for use in infant formulae. Some suitable fat sources include palm oil, high oleic sunflower oil and high oleic safflower oil. The essential fatty acids linoleic and α-linolenic acid may also be added, as well small amounts of oils containing high quantities of preformed arachidonic acid and docosahexaenoic acid such as fish oils or microbial oils. The fat source may have a ratio of n-6 to n-3 fatty acids of about 5:1 to about 15:1; for example about 8:1 to about 10:1.

The nutritional composition of the invention may also contain all vitamins and minerals understood to be essential in the daily diet and in nutritionally significant amounts. Minimum requirements have been established for certain vitamins and minerals. Examples of minerals, vitamins and other nutrients optionally present in the composition of the invention include vitamin A, vitamin B1, vitamin B2, vitamin B6, vitamin B12, vitamin E, vitamin K, vitamin C, vitamin D, folic acid, inositol, niacin, biotin, pantothenic acid, choline, calcium, phosphorous, iodine, iron, magnesium, copper, zinc, manganese, chlorine, potassium, sodium, selenium, chromium, molybdenum, taurine, and L-carnitine. Minerals are usually added in salt form. The presence and amounts of specific minerals and other vitamins will vary depending on the intended population.

If necessary, the nutritional composition of the invention may contain emulsifiers and stabilisers such as soy, lecithin, citric acid esters of mono- and diglycerides, and the like.

The nutritional composition of the invention may also contain other substances which may have a beneficial effect such as lactoferrin, nucleotides, nucleosides, and the like.

The nutritional composition of the invention may also contain carotenoid(s). In some particular embodiments of the invention, the nutritional composition of the invention does not comprise any carotenoid.

The nutritional composition according to the invention may be prepared in any suitable manner. A composition will now be described by way of example.

For example, a formula such as an infant formula may be prepared by blending together the protein source, the carbohydrate source and the fat source in appropriate proportions. If used, the emulsifiers may be included at this point. The vitamins and minerals may be added at this point but they are usually added later to avoid thermal degradation. Any lipophilic vitamins, emulsifiers and the like may be dissolved into the fat source prior to blending. Water, preferably water which has been subjected to reverse osmosis, may then be mixed in to form a liquid mixture. The temperature of the water is conveniently in the range between about 50° C. and about 80° C. to aid dispersal of the ingredients. Commercially available liquefiers may be used to form the liquid mixture.

The fucosylated oligosaccharide(s) may be added at this stage, especially if the final product is to have a liquid form. If the final product is to be a powder, they may likewise be added at this stage if desired.

The liquid mixture is then homogenised, for example in two stages.

The liquid mixture may then be thermally treated to reduce bacterial loads, by rapidly heating the liquid mixture to a temperature in the range between about 80° C. and about 150° C. for a duration between about 5 seconds and about 5 minutes, for example. This may be carried out by means of steam injection, an autoclave or a heat exchanger, for example a plate heat exchanger.

Then, the liquid mixture may be cooled to between about 60° C. and about 85° C. for example by flash cooling. The liquid mixture may then be again homogenised, for example in two stages between about 10 MPa and about 30 MPa in the first stage and between about 2 MPa and about 10 MPa in the second stage. The homogenised mixture may then be further cooled to add any heat sensitive components, such as vitamins and minerals. The pH and solids content of the homogenised mixture are conveniently adjusted at this point.

If the final product is to be a powder, the homogenised mixture is transferred to a suitable drying apparatus such as a spray dryer or freeze dryer and converted to powder. The powder should have a moisture content of less than about 5% by weight. The fucosylated oligosaccharide(s) may also or alternatively be added at this stage by dry-mixing or by blending them in a syrup form of crystals, along with the probiotic strain(s) (if used), and the mixture is spray-dried or freeze-dried.

If a liquid composition is preferred, the homogenised mixture may be sterilised then aseptically filled into suitable containers or may be first filled into the containers and then retorted.

In another embodiment, the composition of the invention may be a supplement.

The supplement may be in the form of tablets, capsules, pastilles or a liquid for example. The supplement may further contain protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste masking agents, weighting agents, jellifying agents and gel forming agents. The supplement may also contain conventional pharmaceutical additives and adjuvants, excipients and diluents, including, but not limited to, water, gelatine of any origin, vegetable gums, lignin-sulfonate, talc, sugars, starch, gum arabic, vegetable oils, polyalkylene glycols, flavouring agents, preservatives, stabilizers, emulsifying agents, buffers, lubricants, colorants, wetting agents, fillers, and the like.

Further, the supplement may contain an organic or inorganic carrier material suitable for oral or parenteral administration as well as vitamins, minerals trace elements and other micronutrients in accordance with the recommendations of Government bodies such as the USRDA.

The nutritional composition according to the invention is for use in infants or young children. The infants or young children may be born term or preterm. In a particular embodiment the nutritional composition of the invention is for use in infants or young children that were born preterm. In a particular embodiment the nutritional composition of the invention is for use in preterm infants.

The nutritional composition of the present invention may also be used in an infant or a young child that was born by C-section or that was vaginally delivered.

In some embodiments the composition according to the invention can be for use before and/or during the weaning period.

The nutritional composition can be administered (or given or fed) at an age and for a period that depends on the needs. The nutritional composition of the present invention may be used for prevention or treatment purposes:
  in preventing and/or treating constipation in an infant or a young child;
  in improving stool consistency in an infant or a young child, e.g. in reducing stool hardness in said infant or young child;
  in improving stool frequency in an infant or a young child, e.g. in regulating/fastening the transit in said infant or young child;
  in preventing and/or treating flatulence, bloating, colics and/or gut discomfort in an infant or young child.

In some embodiments the nutritional composition is used for prevention purposes. The nutritional composition can be for example given immediately after birth of the infants. The composition of the invention can also be given during the first week of life of the infant, or during the first 2 weeks of life, or during the first 3 weeks of life, or during the first month of life, or during the first 2 months of life, or during the first 3 months of life, or during the first 4 months of life, or during the first 6 months of life, or during the first 8 months of life, or during the first 10 months of life, or during the first year of life, or during the first two years of life or even more. In some particularly advantageous embodiments of the invention, the nutritional composition is given (or administered) to an infant within the first 4 or 6 months of birth of said infant.

In some other embodiments, the nutritional composition of the invention is given few days (e.g. 1, 2, 3, 5, 10, 15, 20 . . . ), or few weeks (e.g. 1, 2, 3, 4, 5, 6, 7, 8, 9, 10 . . . ), or few months (e.g. 1, 2, 3, 4, 5, 6, 7, 8, 9, 10 . . . ) after birth. This may be especially the case when the infant is premature, but not necessarily.

In one embodiment the composition of the invention is given to the infant or young child as a supplementary composition to the mother's milk. In some embodiments the infant or young child receives the mother's milk during at least the first 2 weeks, first 1, 2, 4, or 6 months. In one embodiment the nutritional composition of the invention is given to the infant or young child after such period of mother's nutrition, or is given together with such period of mother's milk nutrition. In another embodiment the composition is given to the infant or young child as the sole or primary nutritional composition during at least one period of time, e.g. after the $1^{st}$, $2^{nd}$ or $4^{th}$ month of life, during at least 1, 2, 4 or 6 months.

In one embodiment the nutritional composition of the invention is a complete nutritional composition (fulfilling all or most of the nutritional needs of the subject). In another embodiment the nutrition composition is a supplement or a fortifier intended for example to supplement human milk or to supplement an infant formula or a follow-on formula.

In some other embodiments the nutritional composition of the invention is given for treatment purposes, e.g. when the composition is used for the treatment of constipation In these cases, the nutritional composition of the invention can be given for some days (1, 2, 3, 4, 5, 6 . . . ), or for some weeks (1, 2, 3, 4, 5, 6, 7, 8 or even more), or for some months (1, 2, 3, 4, 5, 6, 7, 8, 9, 10, 11 or even more), depending on the needs. It may be given once the symptoms appear or once these health diseases/conditions have been diagnosed. It may be given up to the symptoms of the treated diseases/conditions disappear, or several days/weeks/months after said disappearance.

In some embodiments, the health benefits/effects are observed during the first few weeks or months of life and/or during the first few weeks or months after administration of the nutritional composition, e.g. during the first week, the first 2 weeks, the first month, the first 2 months, the first 4 months or the first 6 months. Effects at longer term may be less important. In some embodiments, the nutritional composition according to the present invention is for use in improving stool consistency/frequency in an infant during the first month or first 2 months of life and/or after administration of the nutritional composition. In some other embodiments, the nutritional composition according to the present invention is for use in preventing and/or treating colics in infants during the first month, the first 2 months or the first 4 months of life and/or after administration of the nutritional composition, especially in C-section infants.

The present inventors have found that the particular nutritional composition according to the invention is particularly efficient in reducing stool hardness in infants or young children. The nutritional composition was also particularly efficient in terms of flatulence, bloating, colics and gut discomfort since no or a limited level was observed in said infant or young child.

In a particular aspect, the present invention also refers to a nutritional composition comprising at least one fucosylated oligosaccharide for use in reducing stool hardness in an infant or a young child, especially without (i.e. no or in a limited level) any associated flatulence, bloating, colics or gut discomfort.

Other Objects:

Another object of the present invention is the use of at least one fucosylated oligosaccharide in the preparation of a nutritional composition for preventing and/or treating constipation and/or for improving stool consistency/frequency in an infant or young child.

Another object of the present invention is the use of at least one fucosylated oligosaccharide in the preparation of a nutritional composition for preventing and/or treating flatulence, bloating, colics and/or gut discomfort in an infant or a young child, and wherein the fucosylated oligosaccharide(s) is/are in a total amount of 0.8-1.5 g/L of the composition and/or in a total amount of 0.55-1.05 g/100 g of composition on a dry weight basis.

Another object of the present invention is the use of at least one fucosylated oligosaccharide for improving stool consistency/frequency in an infant or young child.

Another object of the present invention is the use of at least one fucosylated oligosaccharide for reducing flatulence, for reducing bloating, for reducing colics and/or for relieving gut discomfort in an infant or young child, and wherein the fucosylated oligosaccharide(s) is/are in a total amount of 0.8-1.5 g/L of the composition and/or in a total amount of 0.55-1.05 g/100 g of composition on a dry weight basis.

The previously-mentioned embodiments and examples (e.g. related to the types and amounts of oligosaccharide, the nutritional composition, the administration, the targeted population . . . ) also apply for these objects (i.e. for these uses).

Another object of the present invention is a pharmaceutical composition comprising at least one fucosylated oligosaccharide for preventing and/or treating constipation and/or for improving stool consistency/frequency, and/or for preventing and/or treating flatulence, bloating, colics and/or gut discomfort in an infant or a young child.

The previously-mentioned embodiments and examples (e.g. related to the types and amounts of oligosaccharide, the administration, the targeted population . . . ) also apply to this object (i.e. pharmaceutical composition).

Another object of the present invention refers to a method for preventing and/or treating constipation and/or for improving stool consistency/frequency in an infant or a young child, said method comprising administering to said infant or young child a nutritional composition comprising at least one fucosylated oligosaccharide.

Another object of the present invention is a method for preventing and/or treating flatulence, bloating, colics and/or gut discomfort in an infant or a young child, said method comprising administering to said infant or young child a nutritional composition comprising at least one fucosylated oligosaccharide, and wherein the fucosylated oligosaccharide(s) is/are in a total amount of 0.8-1.5 g/L of the composition and/or in a total amount of 0.55-1.05 g/100 g of composition on a dry weight basis.

The different embodiments, details and examples previously described in the specification (e.g. related to the types and amounts of oligosaccharide, the nutritional composition, the administration, the targeted population . . . ) also apply to these objects (i.e. methods).

EXAMPLES

The following examples illustrate some specific embodiments of the composition for use according to the present invention. The examples are given solely for the purpose of illustration and are not to be construed as limitations of the present invention.

Example 1

An example of the composition of a nutritional composition (e.g. an infant formula) according to the present invention is given in the below table 1. This composition is given by way of illustration only.

TABLE 1 an example of the composition of a nutritional composition (e.g. an infant formula) according to the present invention

| Nutrients | per 100 kcal | per litre |
|---|---|---|
| Energy (kcal) | 100 | 670 |
| Protein (g) | 1.83 | 12.3 |
| Fat (g) | 5.3 | 35.7 |
| Linoleic acid (g) | 0.79 | 5.3 |
| α-Linolenic acid (mg) | 101 | 675 |
| Lactose (g) | 11.2 | 74.7 |
| Minerals (g) | 0.37 | 2.5 |
| Na (mg) | 23 | 150 |
| K (mg) | 89 | 590 |
| Cl (mg) | 64 | 430 |
| Ca (mg) | 62 | 410 |
| P (mg) | 31 | 210 |
| Mg (mg) | 7 | 50 |
| Mn (μg) | 8 | 50 |
| Se (μg) | 2 | 13 |
| Vitamin A (μg RE) | 105 | 700 |
| Vitamin D (μg) | 1.5 | 10 |
| Vitamin E (mg TE) | 0.8 | 5.4 |
| Vitamin K1 (μg) | 8 | 54 |
| Vitamin C (mg) | 10 | 67 |
| Vitamin B1 (mg) | 0.07 | 0.47 |
| Vitamin B2 (mg) | 0.15 | 1.0 |
| Niacin (mg) | 1 | 6.7 |
| Vitamin B6 (mg) | 0.075 | 0.50 |
| Folic acid (μg) | 9 | 60 |
| Pantothenic acid (mg) | 0.45 | 3 |
| Vitamin B12 (μg) | 0.3 | 2 |
| Biotin (μg) | 2.2 | 15 |
| Choline (mg) | 10 | 67 |
| Fe (mg) | 1.2 | 8 |
| I (μg) | 15 | 100 |
| Cu (mg) | 0.06 | 0.4 |
| Zn (mg) | 0.75 | 5 |
| Oligosaccharides 2FL (g) (HMOs) | 0.15 | 1 |

Example 2

Description of the Study

A controlled, single-blind, randomized, multi-center, interventional clinical trial of 2 groups in parallel was made. Infants were recruited and randomized to one of the 2 study arms within 14 days after birth. The study arms consisted of a classical infant starter formula without HMO [Control] or this classical infant starter formula supplemented with 2 HMOs [HMO]. The composition of the tested infant formula with or without the addition of HMOs was equivalent to the composition shown in table 1, except that:

the control infant formula contained no oligosaccharides/ HMOs (i.e. no 2'Fucosyllactose and no lacto-N-neotetraose);

the tested infant formula with HMOs contained 2'Fucosyllactose but in an amount of 1.24 g/L (corresponding to an amount of 0.86 g/100 g powder before reconstitution; reconstitution was 129.18 g powder/900 mL) and lacto-N-neotetraose but in an amount of 0.63 g/L (corresponding to 0.44 g/100 g powder before reconstitution; reconstitution was 129.18 g powder/900 mL).

Introduction of weaning food was from 4 months onwards.

The study consists of a 6 months±7 days treatment period with one of the two treatments and a 6 months follow-up period without treatment.

Findings

Figure 1A:
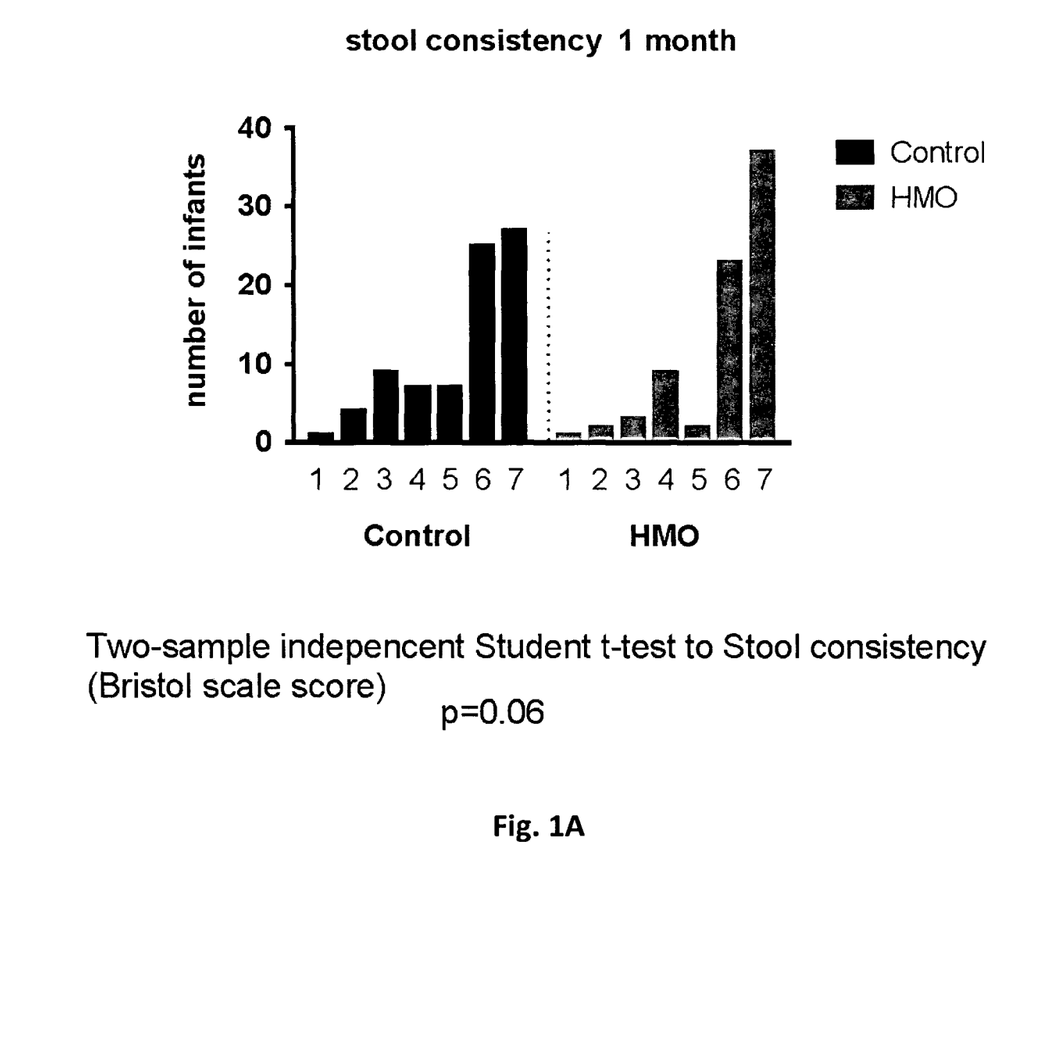
Figure 1B:
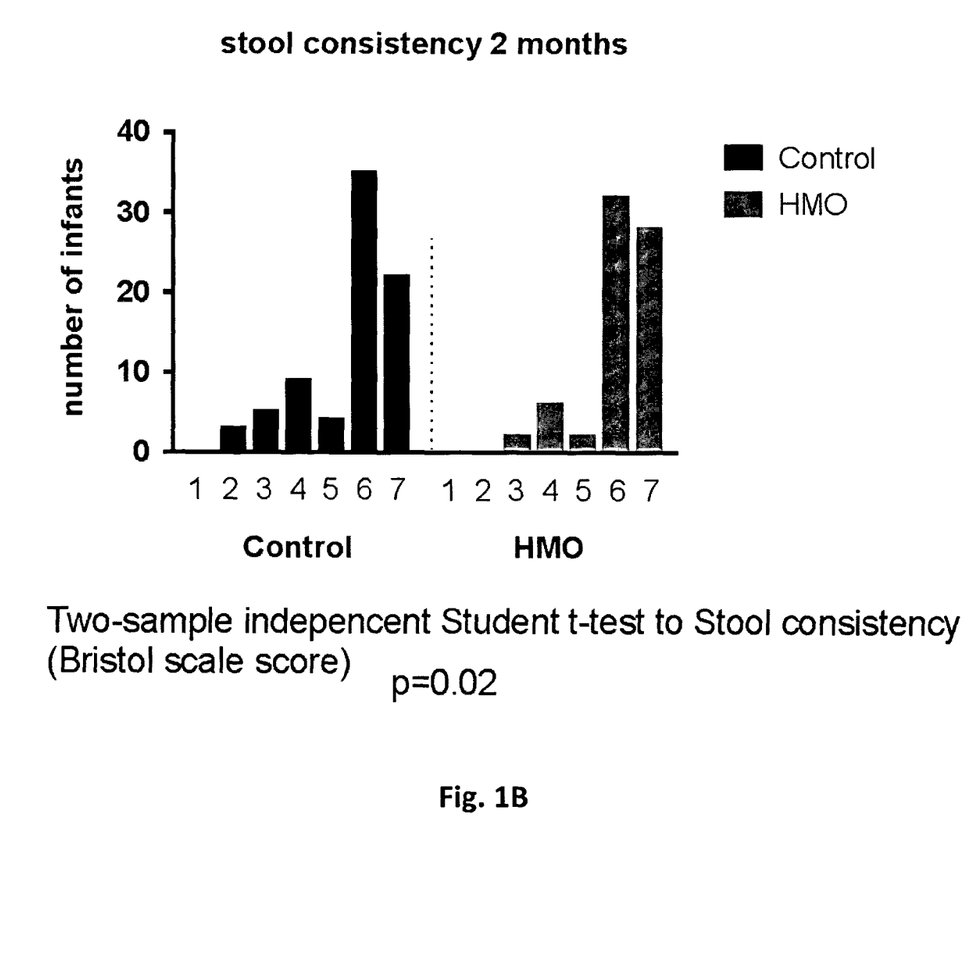

The inventors surprisingly observed that infants of the HMO group (i.e. those fed a classical formula supplemented with 1.24 g/L of 2'-fucosyllactose and 0.63 g/L lacto-N-neotetraose had less hard stools, both at 1 month (FIG. 1A) and 2 months (FIG. 1B) of age. In the same time, no particular issue of flatulence, bloating, colics and gut discomfort was reported in said infant or young child.

Figure 2:
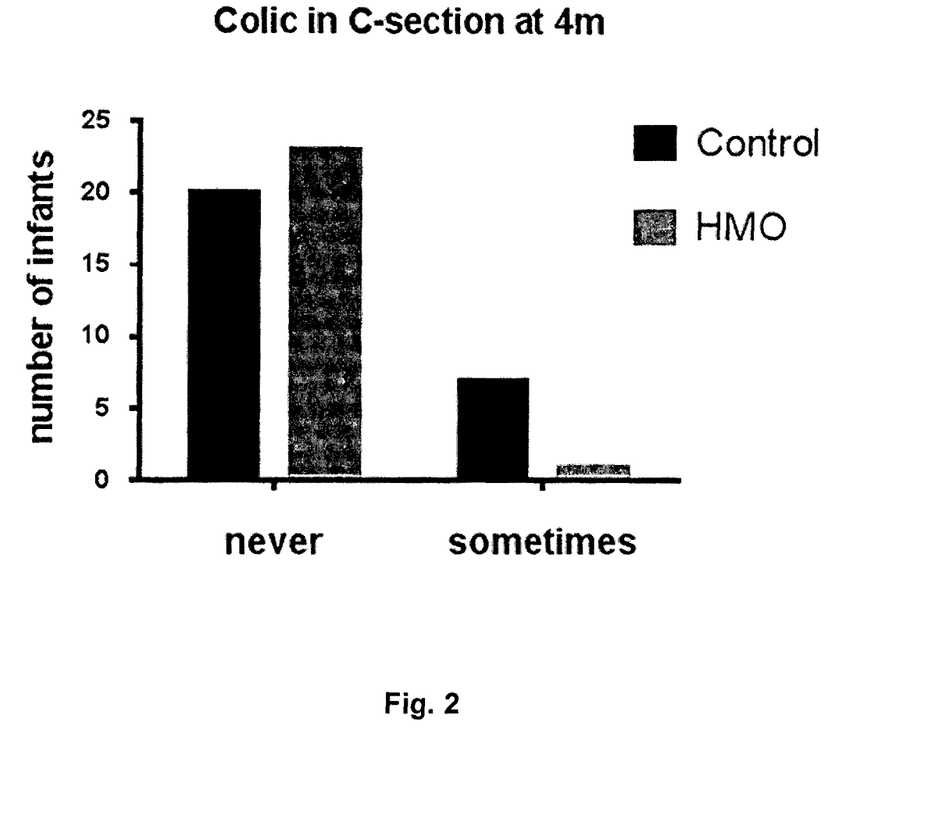
FIG. 2 represents the number of infants born by C-section whose parents reported them to experience 'never' or 'sometimes' Colics at 4 months of age. A linear association analysis for treatment and Colics by visit and delivery mode using Cochran-Mantel-Haenszel test for association showed a significant difference in the C-section group at 4 months of age.

In particular, there was also a significant lower level of colics in infants fed the HMOs born form C-section at 4 months of age, see FIG. 2.

A composition comprising at least one fucosylated oligosaccharide and at least one N-acetylated oligosaccharide is therefore very efficient in infants for use in improving stool consistency, and therefore in improving stool frequency, in preventing and/or treating constipation but also in preventing and/or treating flatulence, bloating, colics and/or gut discomfort in said infants.

In view of the findings of example 3, but without being bound by theory, it is believed that the fucosylated oligosaccharide is the key ingredient of said oligosaccharide mixture that allows getting such effects. So a composition comprising at least one fucosylated oligosaccharide would therefore be efficient in infants for use in improving stool consistency, in improving stool frequency, in preventing and/or treating constipation but also in preventing and/or treating flatulence, bloating, colics and/or gut discomfort in said infants.

Example 3

Description of the Study

The trial population consists of healthy term infants (both male and female) who are post-natal age between 0 and 14 days at enrolment (date of birth=day 0). The following parameters are assessed: stool patterns (stool frequency and consistency), fecal microbiota composition and diversity (including potentially beneficial and potentially pathogenic bacteria and viruses), fecal markers of gut health, GI tolerance including GI symptoms and GI related behaviors.

Stool patterns: including stool frequency and stool consistency

Data collected at Study Day 1, 30, 60, 90, 120, and 180.

Stool consistency is reported as mean stool consistency from the 3-day GI Symptom and Behavior Record using a published, validated 5-point stool scale developed for infants ≤1 year (1=watery, 2=runny, 3=mushy soft, 4=formed, 5=hard), and is also reported as the percentage of stools in each of the 5 stool consistency categories.

GI tolerance: including GI symptoms and GI-related behaviors

Data collected at Study Day 1, 30, 60, 90, 120, and 180.

GI symptoms are reported as frequency of spitting-up/vomiting, and flatulence from the 3-day GI Symptom and Behavior Record GI-related behaviors are reported as mean duration of crying and fussiness (min) as well as sleeping (min), and the frequency of excessive crying (defined as crying greater than 2.25 hours or 140 minutes per day [52, 53]) as reported from the 3-day GI Symptom and Behavior Record.

Fecal microbiota composition and diversity

Stool sample collected at Study Day 1, 120 and 180.

Fecal microbiota composition and diversity (including levels of potentially beneficial and potentially pathogenic bacteria and viruses) are assessed using shotgun metagenomics sequencing to sample all genes in all organisms and high throughput sequencing of the 16S ribosomal genes to provide taxonomic composition and diversity metrics, while quantitative changes in specific bacterial and viral targets including pathogenic bacterial species and viruses are assessed using quantitative polymerase chain reaction (qPCR). qPCR targets may include *Lactobacillus reuteri, Campylobacter jejuni,* Enteropathogenic *Escherichia coli* (EPEC), *Clostridium difficile, Clostridium perfringens, Klebsiella pneumoniae.* Dry stool weight are also be calculated to normalize the data.

Fecal markers of gut health

Stool sample collected at Study Day 1, 120 and 180.

Fecal markers of gut health include secretory IgA [total], human B defensin-2, myeloperoxidase, and lactoferrin.

Incidence of reported Adverse Events AEs (including common illnesses of interest identified using a standardized AE Criteria) and reported use of Concomitant Medications or Non-Pharamacologic Treatments of Interest.

Data collected on Study Day 1 through the 2 weeks post-study telephone contact on Study Day 194. Note: the Infant Health Record is a worksheet completed by the parent anytime the child is ill or takes a medication or visits a health care provider for any reason during the study. The worksheet is used a tool to aid in the completion of the Adverse Event Guidance Forms (used to improve the accuracy of coding for specific Adverse Events of interest) and ultimately the Adverse Event reporting as well as the Medication, and Non-pharmacologic treatment records.

Reported AEs and Serious Adverse Events (SAEs) including type, incidence, severity, seriousness and relation to feeding.

Counts of incident cases as well as cumulative incidence (calculated as described below) and duration will be summarized from Study Day 1 to 120, from Study Day 1 to 180, and from Study Day 1 to 194.

Dose Regimen

The randomized, double-blinded, controlled interventional clinical trial design is the most appropriate to evaluate the growth, safety, and efficacy of the experimental formula (EF) supplemented with 2'FL as compared to control formula (CF).

There were 3 groups:

CF group: healthy term exclusively formula-fed infants. The formula was the CF=Lactogen formula, provided by Nestle SA.

EF group: healthy term exclusively formula-fed infants. The formula was the EF=Lactogen formula (provided by Nestle SA) supplemented by a 2'FL dose of 1 g/L.

BF group: healthy term exclusively breast-fed infants.

Lactogen formula includes *Lactobacillus* probiotic strain in a quantity of $10^6$ cfu/g of said formula (dry weight).

Results

Tested parameters for the EF group are better than for the CF group and results tend to get closer to the ones obtained for the BF group.

The invention claimed is:

1. A method for treating constipation in an infant or a young child in need thereof, the method comprising
administering a nutritional composition comprising human milk oligosaccharides (HMOs) comprising at least one fucosylated oligosaccharide to the infant or young child,
wherein the HMOs are the only oligosaccharides in the nutritional composition, the nutritional composition does not contain non-HMO polysaccharides or non-HMO oligosaccharides, and the nutritional composition does not contain any sialylated oligosaccharide,
the at least one fucosylated oligosaccharide is in a total amount of 1-1.25 g/L of the nutritional composition and/or in a total amount of 0.69-0.87 g/100 g of the nutritional composition on a dry weight basis, and
the nutritional composition is selected from the group consisting of an infant formula, a starter infant formula, a follow-on infant formula, a follow-up infant formula, a fortifier and a supplement.

2. A method for treating hard stool in an infant or a young child in need thereof, the method comprising
administering a nutritional composition comprising human milk oligosaccharides (HMOs) comprising at least one fucosylated oligosaccharide,
wherein the HMOs are the only oligosaccharides in the nutritional composition, the nutritional composition does not contain non-HMO polysaccharides or non-HMO oligosaccharides, and the nutritional composition does not contain any sialylated oligosaccharide,
the at least one fucosylated oligosaccharide is in a total amount of 1-1.25 g/L of the nutritional composition and/or in a total amount of 0.69-0.87 g/100 g of the nutritional composition on a dry weight basis to the infant or young child in need of same, and
the nutritional composition is selected from the group consisting of an infant formula, a starter infant formula, a follow-on infant formula, a follow-up infant formula, a fortifier and a supplement.

3. The method according to claim 1 wherein the at least one fucosylated oligosaccharide is selected from the group consisting of 2'-fucosyllactose, 3'fucosyllactose, difucosyllactose, lacto-N-fucopentaose I, lacto-N-fucopentaose II, lacto-N-fucopentaose III, lacto-N-fucopentaose V, lacto-N-fucohexaose, lacto-N-difucohexaose I, fucosyllacto-N-hexaose, fucosyllacto-N-neohexaose I, fucosyllacto-N-neohexaose II, difucosyllacto-N-hexaose I, difucosyllacto-N-neohexaose I, difucosyllacto-N-neohexaose II, fucosyl-para-Lacto-N-hexaose, and any combination thereof.

4. The method according to claim 1, wherein the at least one fucosylated oligosaccharide comprises a 2' fucosyl-epitope.

5. The method according to claim 1, wherein the at least one fucosylated oligosaccharide is 2'-fucosyllactose (2'FL).

6. The method according to claim 1, wherein the composition further comprising at least one probiotic microorganism.

7. The method according to claim 1, wherein the composition does not comprise any N-acetylated oligosaccharides.

8. The method according to claim 2, wherein the at least one fucosylated oligosaccharide is selected from the group consisting of 2'-fucosyllactose, 3'fucosyllactose, difucosyllactose, lacto-N-fucopentaose I, lacto-N-fucopentaose II, lacto-N-fucopentaose III, lacto-N-fucopentaose V, lacto-N-fucohexaose, lacto-N-difucohexaose I, fucosyllacto-N-hexaose, fucosyllacto-N-neohexaose I, fucosyllacto-N-neohexaose II, difucosyllacto-N-hexaose I, difucosyllacto-N-neohexaose I, difucosyllacto-N-neohexaose II, fucosyl-para-Lacto-N-hexaose, and any combination thereof.

9. The method according to claim 2, wherein the at least one fucosylated oligosaccharide is 2'-fucosyllactose (2'FL).

10. The method according to claim 2, wherein the composition further comprising at least one probiotic microorganism.

11. The method according to claim 2, wherein the composition does not comprise any N-acetylated oligosaccharides.

* * * * *